United States Patent
Bae et al.

(10) Patent No.: US 10,081,804 B2
(45) Date of Patent: Sep. 25, 2018

(54) CARRIER INCLUDING AMMONIUM OXIDIZING BACTERIA IMMOBILIZED THEREIN AND METHOD FOR PREPARING SAME

(71) Applicant: KOREA INSTITUTE OF SCIENCE AND TECHNOLOGY, Seoul (KR)

(72) Inventors: Hyokwan Bae, Seoul (KR); Seockheon Lee, Seoul (KR); Yunchul Chung, Seoul (KR); Jin Young Jung, Daegu (KR); Dae Hee Choi, Daegu (KR); Dong Ryeol Lee, Daegu (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/361,539

(22) Filed: Nov. 28, 2016

(65) Prior Publication Data

US 2017/0355979 A1    Dec. 14, 2017

(30) Foreign Application Priority Data

Jun. 13, 2016  (KR) .................. 10-2016-0073109

(51) Int. Cl.
*C12N 11/10* (2006.01)
*C02F 3/28* (2006.01)
(Continued)

(52) U.S. Cl.
CPC .............. *C12N 11/10* (2013.01); *C02F 3/104* (2013.01); *C02F 3/106* (2013.01); *C02F 3/108* (2013.01); *C02F 3/2806* (2013.01); *C12N 11/04* (2013.01); *C12N 11/08* (2013.01); *C02F 2101/16* (2013.01)

(58) Field of Classification Search
CPC .......... C12N 11/10; C12N 11/04; C12N 11/08
See application file for complete search history.

(56) References Cited

FOREIGN PATENT DOCUMENTS

| EP | 2 735 608 A1 | 5/2014 |
|---|---|---|
| KR | 10-0684603 B1 | 2/2007 |

(Continued)

OTHER PUBLICATIONS

Bae, Hyokwan; et al; "Enrichment of ANAMMOX bacteria from conventional activated sludge entrapped in poly(vinyl alcohol)/sodium alginate gel" Chemical Engineering Journal, 281, 531-540, 2015 (Year: 2015).*

(Continued)

*Primary Examiner* — David W Berke-Schlessel
(74) *Attorney, Agent, or Firm* — NSIP Law

(57) ABSTRACT

Disclosed is a method for preparing the same. The method for preparing a carrier including ammonium oxidizing bacteria immobilized therein includes: preparing a PVA-alginate mixed solution containing PVA mixed with alginate; adding sludge containing ammonium oxidizing bacteria and sodium bicarbonate ($NaHCO_3$) to the PVA-alginate mixed solution to obtain a foaming-beading solution; and dropping the foaming-beading solution to a saturated boric acid solution to obtain beads including sludge immobilized therein, wherein sodium bicarbonate ($NaHCO_3$) is decomposed to produce carbon dioxide ($CO_2$) which is discharged to the exterior of the beads to form pores in the beads, when the foaming-beading solution is dropped to the saturated boric acid solution to obtain beads including sludge immobilized therein.

13 Claims, 8 Drawing Sheets

(51) Int. Cl.
*C02F 3/10* (2006.01)
*C02F 101/16* (2006.01)
*C12N 11/04* (2006.01)
*C12N 11/08* (2006.01)

(56) References Cited

FOREIGN PATENT DOCUMENTS

| KR | 10-2009-0028477 A | 3/2009 |
|----|-------------------|--------|
| KR | 10-1040518 B1 | 6/2011 |
| KR | 10-1126097 B1 | 3/2012 |
| KR | 10-2014-0067271 A | 6/2014 |
| KR | 10-2015-0056259 A | 5/2015 |

OTHER PUBLICATIONS

Li-Sheng, Zhang; et al; "Immobilization of activated sludge using improved polyvinyl alcohol (PVA) gel" Journal of Environmental Science, 19, 1293-1297, 2007 (Year: 2007).*

Park, Byung-Ki, et al., "Microbe Inhabitation Characteristics of Environment-Friendly Hybrid Media Composed of Polymer and Inorganic Material." *Korean Society of Environmental Engineers 2005 Fall Meeting* (2005). (21 pages, with English translation).

Lee, Jintae, et al. "Removal of Nitrogen in Wastewater by Polyvinyl Alcohol (PVA)—Immobilization of Effective Microorganisms." *Korean Journal of Chemical Engineering* 27.1 (2010): 193-197. (5 pages, in English)

Korean Office Action dated Jul. 12, 2017 in corresponding Korean Patent Application No. 10-2016-0073109 (8 pages with English translation).

Van der Star, Wouter RL, et al. "Startup of reactors for anoxic ammonium oxidation: experiences from the first full-scale anammox reactor in Rotterdam." Water research 41.18 (2007): 4149-4163. (15 pages in English)

* cited by examiner

| | | Picture of the expanded bead | Diameter (mm) | | Expansion ratio (%) | Break point (L min$^{-1}$) |
|---|---|---|---|---|---|---|
| | | | initial | final | | |
| Control | |  | 4.49 ±0.31 | 13.48 ±0.10 | 300 | 1.5 |
| NaHCO$_3$ (w/v %) | 0.15 |  | 4.86 ±0.18 | 9.03 ±0.40 | 186 | 1.5 |
| | 0.30 |  | 4.56 ±0.23 | 5.87 ±0.47 | 129 | > 5.0 |
| | 0.60 |  | 4.71 ±0.20 | 5.60 ±0.26 | 119 | > 5.0 |
| | 1.20 |  | 4.74 ±0.22 | 5.62 ±0.20 | 119 | > 5.0 |

CARRIER INCLUDING AMMONIUM OXIDIZING BACTERIA IMMOBILIZED THEREIN AND METHOD FOR PREPARING SAME

CROSS-REFERENCE TO RELATED APPLICATION

This application claims priority to Korean Patent Application No. 10-2016-0073109, filed on Jun. 13, 2016, and all the benefits accruing therefrom under 35 U.S.C. § 119, the contents of which in its entirety are herein incorporated by reference.

BACKGROUND

1. Field

The present disclosure relates to a carrier including ammonium oxidizing bacteria immobilized therein and a method for preparing the same. More particularly, the present disclosure relates to a carrier including ammonium oxidizing bacteria immobilized therein, which is obtained by converting sludge containing anaerobic ammonium oxidizing bacteria or aerobic ammonium oxidizing bacteria into beads and is capable of improving gas permeability and strength, and a method for preparing the same.

2. Description of the Related Art

As a method for removing nitrogen in sewage and wastewater, a biological process based on nitrification and heterotrophic denitrification has been used widely. According to the conventional biological process, nitrification is carried out by oxidation of ammonia and oxidation of nitrite sequentially. Herein, when oxidizing nitrogen through oxidation of ammonia and oxidation of nitrite, a large amount of oxygen is required. In addition, heterotrophic denitrification in a biological process requires supply of an organic carbon source as an electron donor of bacteria in order to reduce nitrite or nitrate. Although relatively inexpensive methanol has been used generally as an organic carbon source, continuous supply of methanol is required, and thus there is a burden on operation cost.

To solve such a problem of a biological process, many studies have been conducted recently about a method for removing nitrogen by using anaerobic ammonium oxidizing bacteria (see, Korean Patent Publication No. 10-1040518). Anaerobic ammonium oxidizing bacteria are autotrophic bacteria using ammonium ($NH_4^+$) and nitrite ($NO_2^-$) as substrates to produce dinitrogen gas ($N_2$) under an anaerobic condition. Since anaerobic ammonium oxidizing bacteria use ammonium ($NH_4^+$) as an electron donor and nitrite ($NO_2^-$) as an electron acceptor, there is no need for addition of an organic carbon source, unlike the conventional biological process. In addition, there is an advantage in that the amount of oxygen required for partial nitrification of ammoniacal nitrogen is reduced by about 40% as compared to the conventional biological process, and thus the cost required for aeration and carbon source supply is saved.

In addition, an autotrophic denitrification process using anaerobic ammonium oxidizing bacteria shows significantly higher denitrification efficiency of 26-42 kg·N/m³·day, as compared to the conventional biological process which provides the maximum heterotrophic denitrification efficiency of at most 3 kg·N/m³·day.

Meanwhile, five major genera of anaerobic ammonium oxidizing bacteria, *Candidatus Brocadia, Candidatus Kuenenia, Candidatus Scalindua, Candidatus Anammoxoglobus* and *Candidatus Jettenia*, have been found in wastewater treatment processes and natural environments, and they characteristically show a very low growth rate, i.e., a doubling time of about 11 days. Thus, it is reported that a long start-up period is required to allow autotrophic denitrification based on anaerobic ammonium oxidizing bacteria to proceed to a predetermined level, and continuous additional introduction of anaerobic ammonium oxidizing bacteria for at least 1 year is required after the anaerobic ammonium oxidizing bacteria are applied first (Van der Star W R, Abma W R, Blommers D, Mulder J W, Tokutomi T, Strous M, Picioreanu C, van Loosdrecht M C (2007) Startup of reactors for anoxic ammonium oxidation: experiences from the first full-scale anammox reactor in Rotterdam. Water Research 41:4149-4163). For reference, aerobic ammonium oxidizing bacteria show a doubling time of 8 hours, which is faster than the growth rate of anaerobic ammonium oxidizing bacteria but significantly slower than the general aerobic bacteria.

The start-up period of an anaerobic ammonium oxidation process is affected by the configuration of a reactor, quality of influent, stability of process conditions, or the like. Among those, the most important factor is immobilization technology for retaining anaerobic ammonium oxidizing bacteria in a reactor. Currently, the most widely used immobilization technology is a method for accelerating aggregation to induce granulation. However, it is required to maintain a significantly complicated operating condition to carry out aggregation of bacteria. In addition, after the lapse of 3-6 months required for aggregation, additional cost and time are required to increase the amount of aggregated granular sludge. Thus, it is not adequate to obtain a large amount of anaerobic ammonium oxidizing bacteria at an early stage.

More recently, a method for immobilizing anaerobic ammonium oxidizing bacteria by using a synthetic polymer has been suggested. The present applicant has suggested a method for cultivating anaerobic ammonium oxidizing bacteria by converting active sludge containing anaerobic ammonium oxidizing bacteria into beads through Korean Patent Application No. 10-2014-185833.

One of the factors to be considered when immobilizing anaerobic ammonium oxidizing bacteria by using a synthetic polymer, such as poly(vinyl alcohol) (PVA), is the gas permeability and strength of a carrier.

The anaerobic ammonium oxidizing bacteria immobilized in a carrier produce dinitrogen gas ($N_2$) while they are grown with ammonium and nitrite as substrates. It is required to discharge the produced dinitrogen gas smoothly to the exterior. When such dinitrogen gas is not discharged, the carrier may be swelled and broken. To discharge such dinitrogen gas smoothly, it is required for the carrier to have pores by which the inner part and outer part of the carrier are connected spatially with each other. In addition, the carrier including anaerobic ammonium bacteria immobilized therein should have high physical strength, because they are used for a long time in the reactor.

REFERENCES

Patent Documents

Korean Patent Publication No. 1040518

Non-Patent Documents

Van der Star W R, Abma W R, Blommers D, Mulder J W, Tokutomi T, Strous M, Picioreanu C, van Loosdrecht M C (2007) Startup of reactors for anoxic ammonium oxidation: experiences from the first full-scale anammox reactor in Rotterdam. Water Research 41:4149-4163.

SUMMARY

The present disclosure is directed to providing a carrier including ammonium oxidizing bacteria immobilized therein, which is obtained by converting sludge containing anaerobic ammonium oxidizing bacteria or aerobic ammonium oxidizing bacteria into beads and is capable of improving gas permeability and strength, and a method for preparing the same.

In one aspect, there is provided a method for preparing a carrier including ammonium oxidizing bacteria immobilized therein, which includes: preparing a PVA-alginate mixed solution containing PVA mixed with alginate; adding sludge containing ammonium oxidizing bacteria and sodium bicarbonate ($NaHCO_3$) to the PVA-alginate mixed solution to obtain a foaming-beading solution; and dropping the foaming-beading solution to a saturated boric acid solution to obtain beads including sludge immobilized therein, wherein sodium bicarbonate ($NaHCO_3$) is decomposed to produce carbon dioxide ($CO_2$) which is discharged to the exterior of the beads to form pores in the beads, when the foaming-beading solution is dropped to the saturated boric acid solution to obtain beads including sludge immobilized therein.

According to an embodiment, the foaming-beading solution may include sodium bicarbonate ($NaHCO_3$) in an amount of 0.15-1.2% (w/v), particularly 0.5-0.7% (w/v).

According to another embodiment, the method may further include dipping the beads including the beads immobilized therein in a phosphoric acid solution to increase the mechanical strength.

According to still another embodiment, the foaming-beading solution may include zeolite, and the zeolite may be provided in the beads including the sludge immobilized therein.

According to still another embodiment, the saturated boric acid solution may be controlled to have a pH of 3-4.

According to still another embodiment, the method may further include dipping the beads including the sludge immobilized therein in distilled water to induce swelling of the beads so that sodium bicarbonate ($NaHCO_3$) and unreacted alginate remaining in the beads may be discharged to the exterior of the beads.

According to still another embodiment, the foaming-beading solution may include solid particles, and the solid particles may be detached from the beads to form pores, after the beads including the sludge immobilized therein are obtained. The solid particles may be activated carbon.

According to yet another embodiment, the ammonium oxidizing bacteria may comprise at least one selected from a group comprising anaerobic ammonium oxidizing bacteria and aerobic ammonium oxidizing bacteria.

Alternatively, for the purpose of heterotrophic denitrification, heterotrophic denitrifying bacteria can be used instead of the ammonium oxidizing bacteria in order to remove nitrite or nitrate in the form of dinitrogen gas.

The carrier including ammonium oxidizing bacteria immobilized therein and the method for preparing the same provide the following effect.

Since sodium bicarbonate ($NaHCO_3$) is used when immobilizing ammonium oxidizing bacteria in PVA-alginate based beads, it is possible to improve the gas permeability and strength of the beads.

DETAILED DESCRIPTION

The present disclosure relates to a method for preparing a carrier including ammonium oxidizing bacteria immobilized therein and a method for improving the gas permeability and strength of the carrier.

The ammonium oxidizing bacteria immobilized in the carrier disclosed herein may comprise at least one selected from a group comprising anaerobic ammonium oxidizing bacteria and aerobic ammonium oxidizing bacteria. Particularly, the ammonium oxidizing bacteria may be anaerobic ammonium oxidizing bacteria or aerobic ammonium oxidizing bacteria.

Alternatively, heterotrophic denitrifying bacteria can be used instead of the ammonium oxidizing bacteria in order to remove nitrite or nitrate in the form of dinitrogen gas through a heterotrophic denitrification.

Anaerobic ammonium oxidizing bacteria remove nitrogen in sewage and wastewater through anaerobic ammonium oxidation (Chemical Formula 1), while aerobic ammonium oxidizing bacteria remove ammoniacal nitrogen in sewage and wastewater through nitrification (Chemical Formula 2) and partial nitrification (Chemical Formula 3).

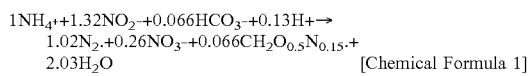   [Chemical Formula 1]

   [Chemical Formula 2]

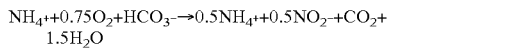

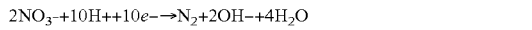

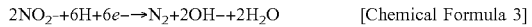   [Chemical Formula 3]

Hereinafter, the carrier including ammonium oxidizing bacteria immobilized therein and the method for preparing the same according to an embodiment of the present disclosure will be explained in more detail with reference to the accompanying drawings.

Figure 1:
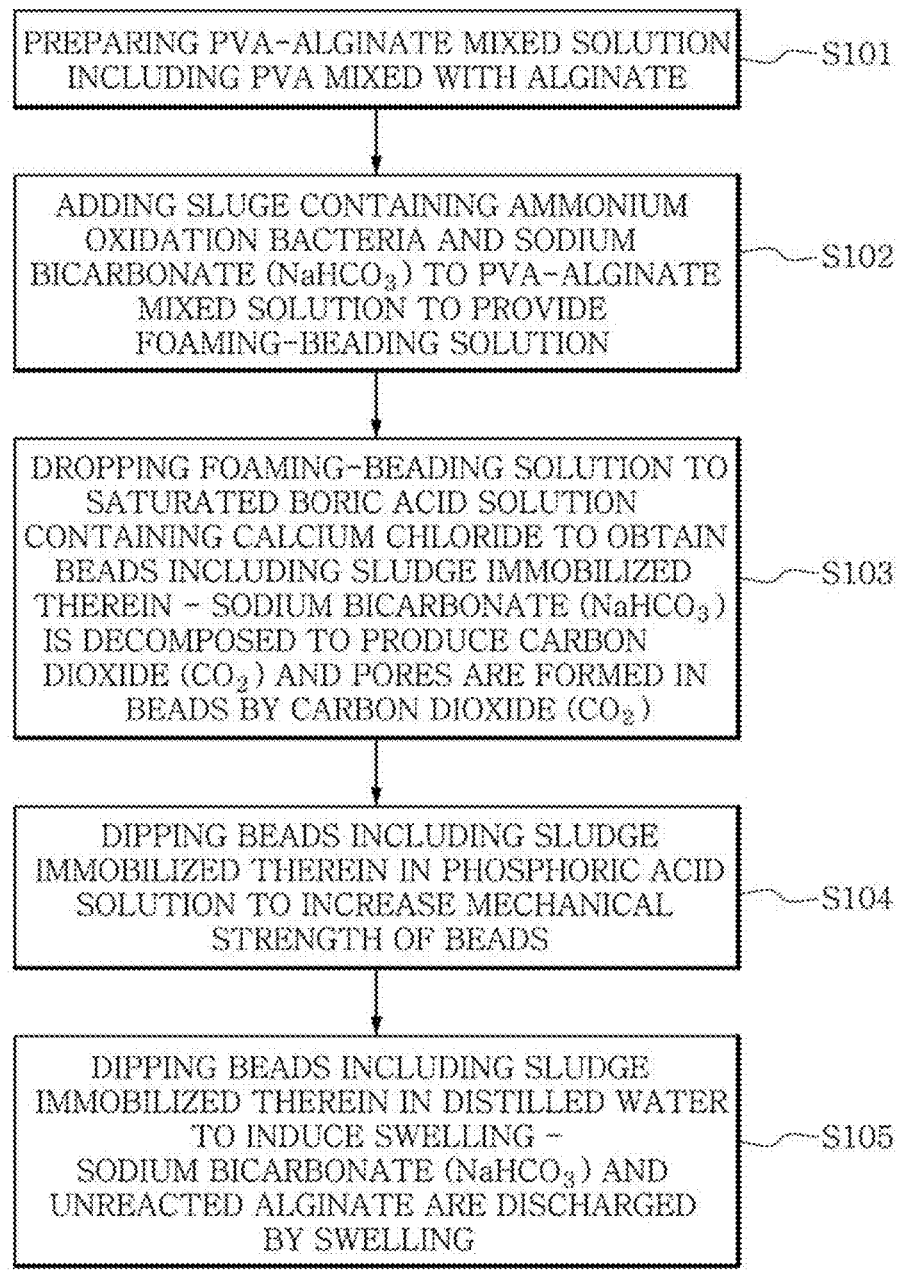
FIG. 1 is a flow chart illustrating the method for preparing a carrier including ammonium oxidizing bacteria immobilized therein according to an embodiment of the present disclosure.

Referring to FIG. 1, a PVA-alginate mixed solution and sludge are prepared individually.

The PVA-alginate mixed solution is one containing polyvinyl alcohol (PVA) mixed with alginate in distilled water (S101). A solution including a mixture of 10-20 g of PVA and 1-5 g of sodium alginate per 100 g of distilled water may be used. To accomplish homogeneous mixing of PVA with alginate, the PVA-alginate mixed solution may be dissolved at a temperature of 100° C. or higher for a predetermined time.

The sludge means one containing ammonium oxidizing bacteria, wherein the ammonium oxidizing bacteria may comprise at least one selected from a group comprising anaerobic ammonium oxidizing bacteria and aerobic ammonium oxidizing bacteria. Alternatively, heterotrophic denitrifying bacteria can be used instead of the ammonium oxidizing bacteria in order to remove nitrite or nitrate in the form of dinitrogen gas through a heterotrophic denitrification.

To improve the biological activity of the prepared beads, highly concentrated sludge may be used and such highly concentrated sludge may be prepared through gravity precipitation and centrifugal separation. In addition, to increase the amount of anaerobic ammonium oxidizing bacteria supported at first, the concentration of volatile suspended solids (VSS) in the sludge may be increased to 5-10 VSS g/L. In addition to this, the sludge may be screened with a sieve having a size of 100-1,000 μm to obtain a uniform size of bacteria.

Then, the PVA-alginate mixed solution is mixed with the sludge. The PVA-alginate mixed solution and the sludge may be mixed at a volume ratio of 1:1-4.

After mixing the PVA-alginate mixed solution with the sludge, sodium bicarbonate ($NaHCO_3$) is further introduced and mixed again (S102). Sodium bicarbonate ($NaHCO_3$) is an inorganic foaming agent and is decomposed under an environment of pH 3-4 to produce carbon dioxide ($CO_2$). Such carbon dioxide ($CO_2$) produced by the decomposition of sodium bicarbonate ($NaHCO_3$) functions to form pores in the beads during the formation of the beads. Hereinafter, the solution in which the PVA-alginate mixed solution, sludge and sodium bicarbonate ($NaHCO_3$) are mixed is referred to as 'foaming-beading solution'. Meanwhile, zeolite may be further introduced to the foaming-beading solution for the purpose of controlling the specific gravity of the beads.

After the solution in which the PVA-alginate mixed solution, sludge and sodium bicarbonate ($NaHCO_3$) are mixed, i.e., the foaming-beading solution is prepared, the viscous foaming-beading solution is dropped to a saturated boric acid ($H_3BO_3$) solution containing calcium chloride ($CaCl_2$). Herein, saturated boric acid ($H_3BO_3$) and calcium chloride ($CaCl_2$) are crosslinking agents for converting the foaming-beading solution into beads. Calcium chloride functions as a crosslinking agent for alginate, while saturated boric acid functions as a crosslinking agent for PVA. Saturated boric acid ($H_3BO_3$) solution contains 0.5-1 g of calcium chloride ($CaCl_2$) per 100 g of distilled water.

Figure 2:
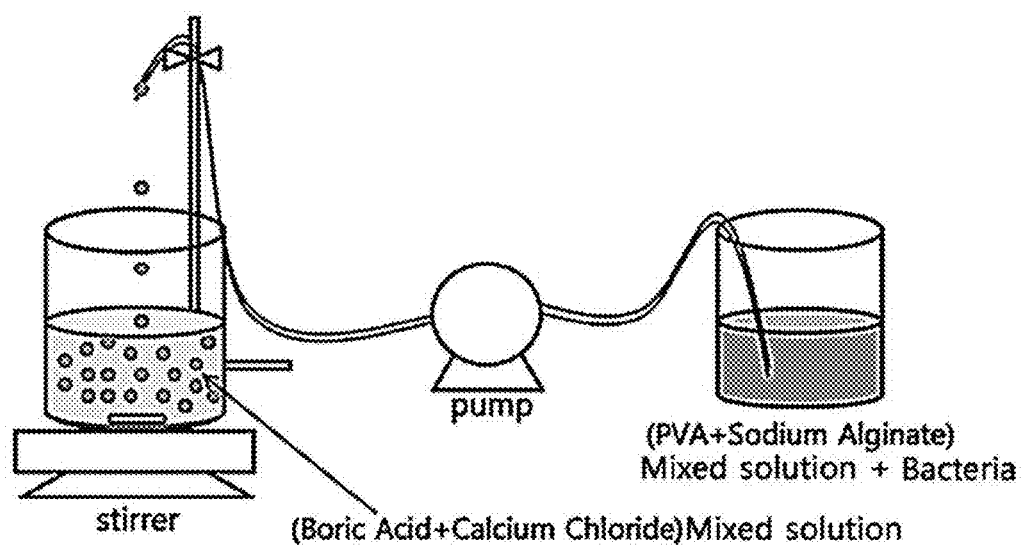
FIG. 2 is a schematic view illustrating the method for preparing a carrier including ammonium oxidizing bacteria immobilized therein according to an embodiment of the present disclosure.

As the foaming-beading solution is dropped to saturated boric acid ($H_3BO_3$) containing calcium chloride ($CaCl_2$), PVA is crosslinked with alginate to form beads, and the sludge is supported in the beads and immobilized therein (S103). For reference, FIG. 2 is a schematic view illustrating the method for preparing a carrier including ammonium oxidizing bacteria immobilized therein according to an embodiment of the present disclosure.

During the formation of the beads, sodium bicarbonate ($NaHCO_3$) contained in the foaming-beading solution is decomposed to produce carbon dioxide ($CO_2$). Such carbon dioxide ($CO_2$) produced by the decomposition of sodium bicarbonate ($NaHCO_3$) is discharged to the exterior of the beads. As carbon dioxide ($CO_2$) in the beads is discharged to the exterior of the beads, pores are formed in the beads.

When the finished beads are used to culture ammonium oxidizing bacteria or the ammonium oxidizing bacteria are used to treat sewage and wastewater, the ammonium oxidizing bacteria, such as anaerobic ammonium oxidizing bacteria in the beads grow with ammonium and nitrite as substrates and produce dinitrogen gas ($N_2$). When dinitrogen gas in the beads is not discharged to the exterior, beads are swelled undesirably. To allow effective discharge of dinitrogen gas, it is required that a dinitrogen gas flow path is provided in the beads. According to an embodiment, sodium bicarbonate ($NaHCO_3$) as an inorganic foaming agent is used to form pores functioning as a dinitrogen gas flow path in the beads. The pores functions not only as a dinitrogen gas flow path but also as a path through which dissolved oxygen is supplied into the beads during nitrification.

Meanwhile, decomposition of sodium bicarbonate ($NaHCO_3$) into carbon dioxide ($CO_2$) is carried out under an environment of pH 3-4. Thus, it is required that the saturated boric acid ($H_3BO_3$) solution containing calcium chloride ($CaCl_2$) is controlled to have pH 3-4.

As mentioned above, sodium bicarbonate ($NaHCO_3$) as an inorganic foaming agent functions to form pores in the beads. Use of inorganic foaming agents other than sodium bicarbonate ($NaHCO_3$), such as calcium carbonate ($CaCO_3$) or sodium carbonate ($Na_2CO_3$), may be considered. However, in the case of calcium carbonate ($CaCO_3$), it has a significantly low solubility of about 1.3-1.5 mg to 100 g of distilled water, and thus is hardly dissolved in the foaming-beading solution. Although it may be dissolved at a very low pH condition (1 or less), such a severely low pH condition adversely affects the activity of bacteria. In addition, in the case of sodium carbonate ($Na_2CO_3$), spherical pores are not formed during the conversion into beads and individual aggregation is poor to cause agglomeration of beads among themselves. Thus, it is difficult to obtain beads, i.e., carrier, having a diameter of 3-7 mm.

Therefore, it is required to use sodium bicarbonate ($NaHCO_3$) to form pores stably while not adversely affecting the activity of bacteria. In addition, sodium bicarbonate ($NaHCO_3$) not only functions to form pores in the beads but also functions to improve the strength of beads. Improvement of the strength of beads accomplished by sodium bicarbonate ($NaHCO_3$) is supported by the following test results as described hereinafter in detail. To satisfy both formation of pores in the beads and improvement of strength of beads, it is required to introduce sodium bicarbonate ($NaHCO_3$) to the foaming-beading solution in an amount of 0.15-1.2% (w/v), particularly 0.5-0.7% (w/v), as described hereinafter in detail with reference to the test results.

Hereinabove, formation of beads in the beads using sodium bicarbonate ($NaHCO_3$) is suggested. However, pore formation may be carried out by using solid particles. A method for forming pores using solid particles will be explained hereinafter.

When the formation of beads is finished while solid particles are incorporated to the foaming-beading solution, the solid particles form no chemical bonding with PVA or alginate, and thus are detached from the beads by external physical impact having a predetermined intensity. Then, pores connecting the inner part of the beads with the outer part thereof are formed at the portions where the solid particles are detached. Herein, the term "physical impact having a predetermined intensity" means the contact among beads caused by the action of an agitator or external physical impact for detaching the solid particles from the beads.

The solid particles may be added to and mixed with the foaming-beading solution, or may be mixed preliminarily with the PVA-alginate mixed solution. In addition, the solid particles may include any materials which do not chemically react with PVA and alginate. According to an embodiment, activated carbon having a size of 10 μm-1 mm or less is used. Further, the solid particles are mixed at a ratio of 0.5-5 g per 100 g of distilled water, based on the case where the solid particles are mixed with the PVA-alginate mixed solution. When the amount of the solid particles in the PVA-alginate mixed solution is larger than 5%, beads are not formed due to an increase in viscosity caused by the solid particles.

As methods for forming pores, use of sodium bicarbonate ($NaHCO_3$) and use of solid particles are suggested. The two methods may be applied individually or in combination.

Meanwhile, when the foaming-beading solution is dropped to the saturated boric acid ($H_3BO_3$) solution containing calcium chloride ($CaCl_2$) to form beads including the sludge immobilized therein, the size of beads may be controlled considering the reaction efficiency of ammonium oxidizing bacteria, or the like. A smaller size of beads provides higher reaction efficiency of ammonium oxidizing bacteria. However, the bead size may be about 1-7 mm in order to prevent leakage of the beads from the reactor. The bead size may be controlled by using a needle, tube or funnel optionally. It is possible to control the mechanical strength through the reaction time between the foaming-beading solution and saturated boric acid solution.

In addition, when the foaming-beading solution is dropped to the saturated boric acid ($H_3BO_3$) solution containing calcium chloride ($CaCl_2$) to form beads including the sludge immobilized therein, the foaming-beading solution may be maintained at a temperature of 30-50° C. When the beads are required to have a much smaller size, the temperature of the foaming-beading solution may be controlled to 70° C. to reduce the viscosity.

After the foaming-beading solution is dropped to the saturated boric acid ($H_3BO_3$) solution containing calcium chloride ($CaCl_2$) to form beads including the sludge immobilized therein, the beads are dipped in 0.5-1M phosphoric acid ($KH_2PO_4$) solution to further reinforce the mechanical strength of the beads (S104).

Then, the beads are washed with distilled water 2-3 times, and dipped in distilled water to cause swelling (S105). Through the swelling, sodium bicarbonate ($NaHCO_3$) and unreacted alginate remaining in the beads are discharged to the exterior. In this manner, the method for preparing a carrier including ammonium oxidizing bacteria immobilized therein is completed.

Hereinabove, the carrier including ammonium oxidizing bacteria immobilized therein and the method for preparing the same according to an embodiment are described. Hereinafter, the present disclosure will be explained in more detail with reference to Examples.

Example 1: Preparation of Carrier

First, 15 g of PVA and 2 g of sodium alginate are mixed per 100 g of distilled water to provide a PVA-alginate mixed solution. Next, sludge containing anaerobic ammonium oxidizing bacteria is added to the PVA-alginate mixed solution. Then, sodium bicarbonate ($NaHCO_3$) is introduced to the PVA-alginate mixed solution mixed with sludge in an amount of 0, 0.15, 0.30, 0.60 or 1.20% (w/v) to provide foaming-beading solutions. After that, each foaming-beading solution is dropped to a saturated boric acid solution containing 0.5-1 g of calcium chloride per 100 g of distilled water to form beads. The beads are allowed to react with 0.5M phosphoric acid solution.

Example 2: Pores and Swelling Property of Carrier

Figure 3:
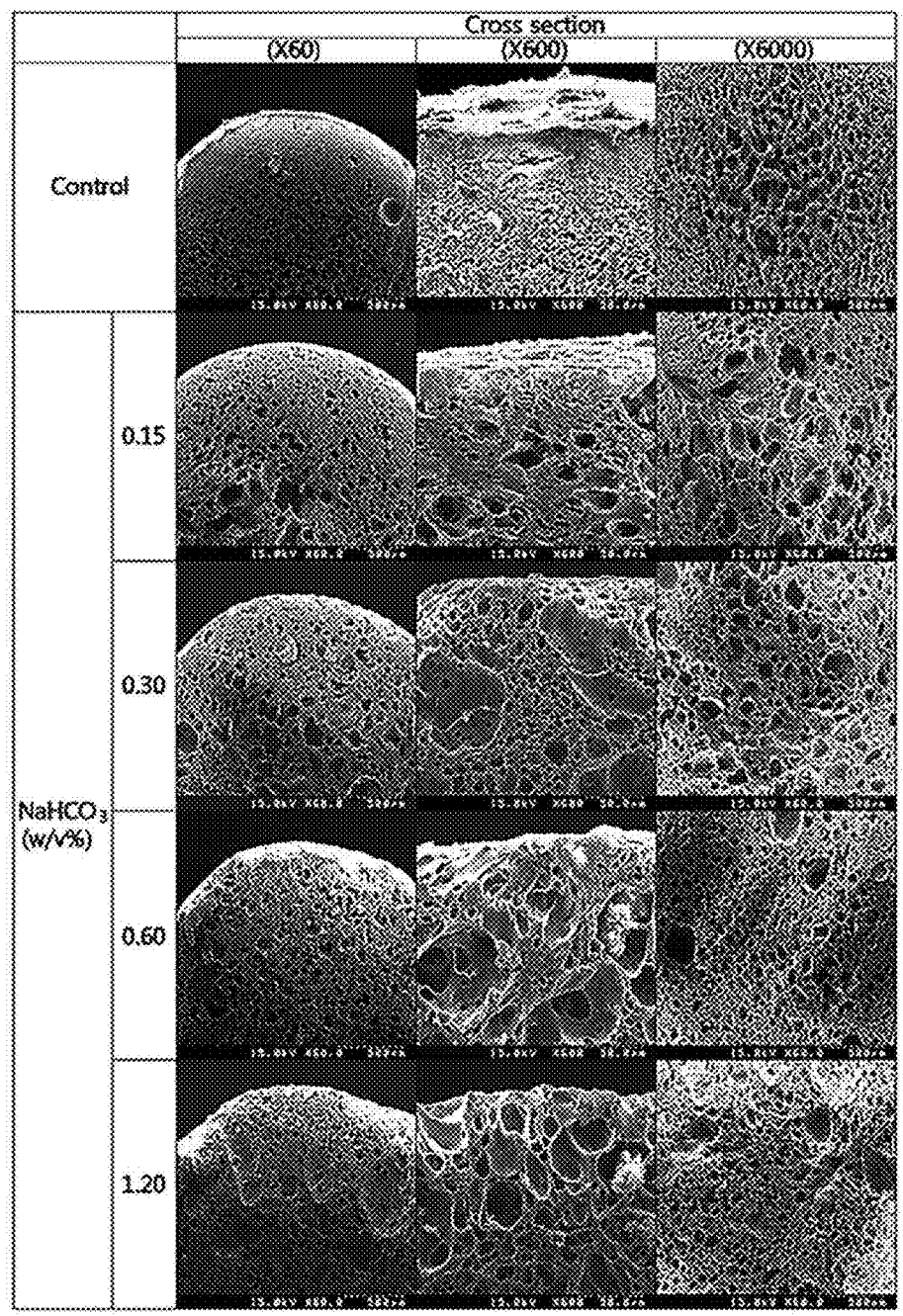
FIG. 3 is a scanning electron microscopic (SEM) image of the beads obtained according to Test Example 1.
Figure 4:
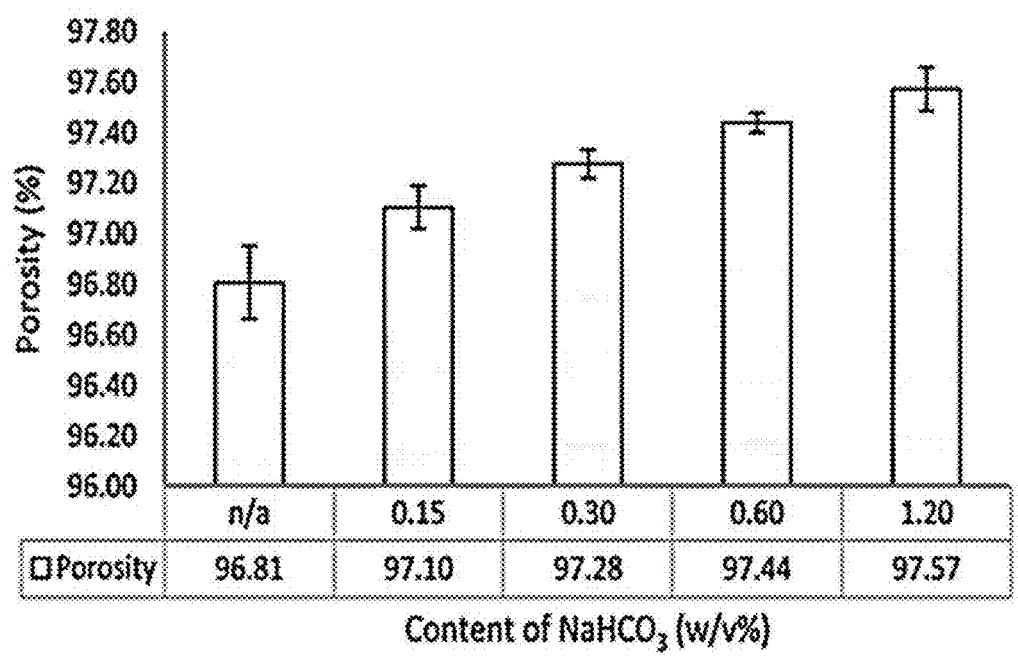
FIG. 4 shows the test results illustrating the porosity of the beads obtained according to Test Example 1.

FIG. 3 is a scanning electron microscopic (SEM) image of the beads obtained according to Example 1. As shown in FIG. 3, in the case of the beads to which no sodium bicarbonate ($NaHCO_3$) is introduced (see, 'control' in FIG. 3), pores are little formed as compared to the beads to which sodium bicarbonate ($NaHCO_3$) is introduced. In addition, as the amount of sodium bicarbonate ($NaHCO_3$) is increased, pore size is increased, as also determined by the porosity test results as shown in FIG. 4. Referring to FIG. 4, as the amount of sodium bicarbonate ($NaHCO_3$) is increased, porosity is increased.

Figure 5:
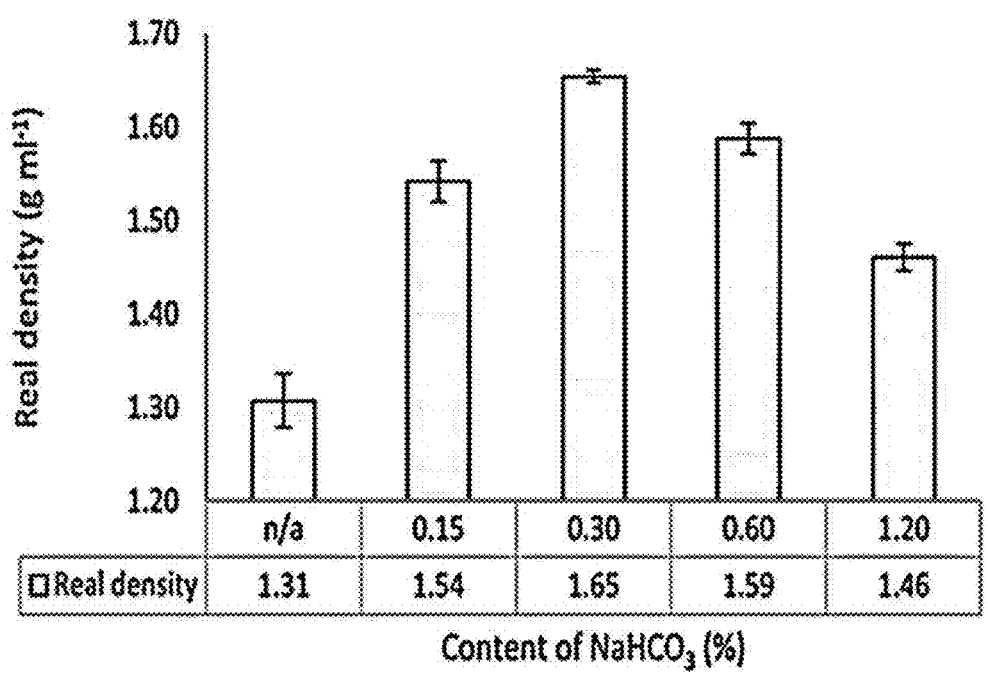
FIG. 5 shows the test results illustrating the density of the beads obtained according to Test Example 1.

Meanwhile, after measuring the density of the beads obtained according to Example 1, it can be seen that the density of the beads is increased as the amount of sodium bicarbonate ($NaHCO_3$) is increased up to 0.3% (w/v) as shown in FIG. 5. However, when the amount of sodium bicarbonate ($NaHCO_3$) is higher than 0.3% (w/v), the density of the beads is decreased. It is thought that this is because the swelling degree is different depending on the amount of sodium bicarbonate ($NaHCO_3$).

Figure 6:
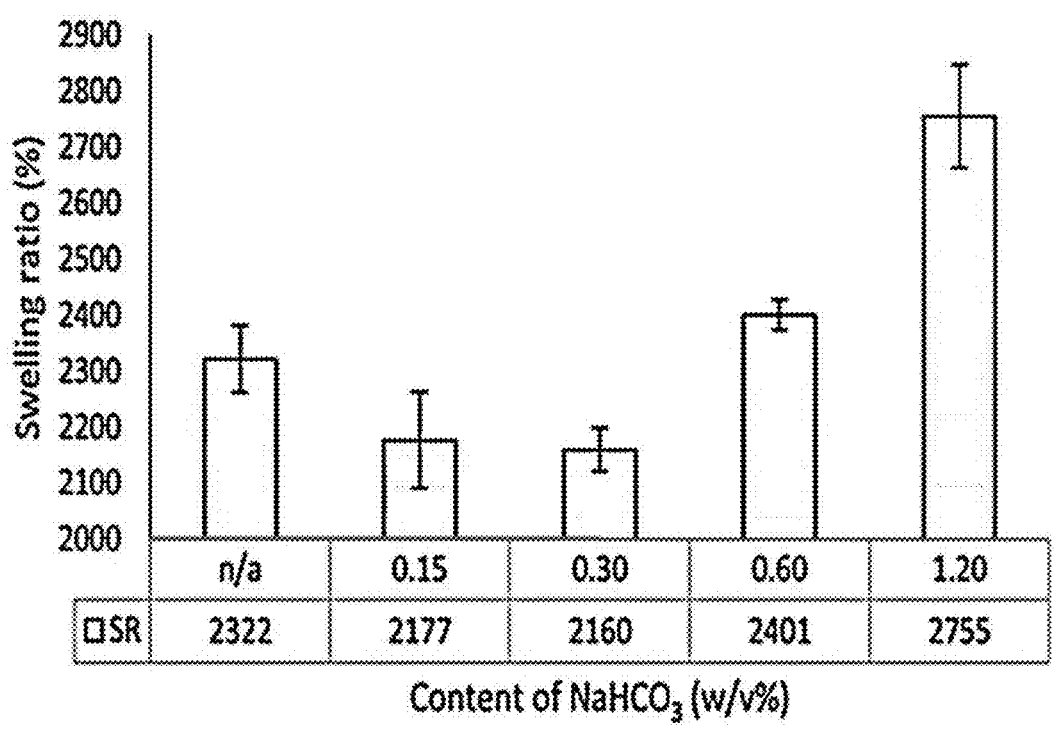
FIG. 6 shows the test results illustrating the swelling degree of the beads obtained according to Test Example 1.

Referring to FIG. 6, it can be seen that when the amount of sodium bicarbonate ($NaHCO_3$) is within a range of 0-0.3% (w/v), a higher amount of sodium bicarbonate ($NaHCO_3$) increases the amount of pores formed inside and outside of the beads, and thus the contact of boric acid solution with the PVA and alginate inside and outside of the beads is improved, resulting in a decrease in swelling degree. On the contrary, it is thought that when the amount of sodium bicarbonate ($NaHCO_3$) is higher than 0.6% (w/v), the swelling degree is increased due to the pores formed additionally.

It can be seen from the results of FIG. 4-FIG. 6, introduction of sodium bicarbonate ($NaHCO_3$) improves the porous property of the beads. In addition, referring to the results of FIG. 5 and FIG. 6, the density of the beads is increased and the swelling degree of the beads is decreased until the amount of sodium bicarbonate ($NaHCO_3$) is up to 0.3% (w/v). This is because sodium bicarbonate ($NaHCO_3$) introduced to the beads causes increased formation of pores and the pores improve the contact property of the boric acid solution with PVA and alginate inside and outside of the beads, resulting in formation of beads with a dense structure. However, when the amount of sodium bicarbonate ($NaHCO_3$) is higher than 0.6% (w/v), the opposite result is obtained. It is thought that this results from additionally formed pores. When the amount of sodium bicarbonate ($NaHCO_3$) is higher than 0.6% (w/v), there is a similar tendency of improvement in contact with the boric acid caused by pore formation.

Therefore, it can be seen from the above results that introduction of sodium bicarbonate ($NaHCO_3$) improves the contact of boric acid solution with PVA and alginate inside and outside of the beads, and thus increases the strength of the beads.

Figure 7:
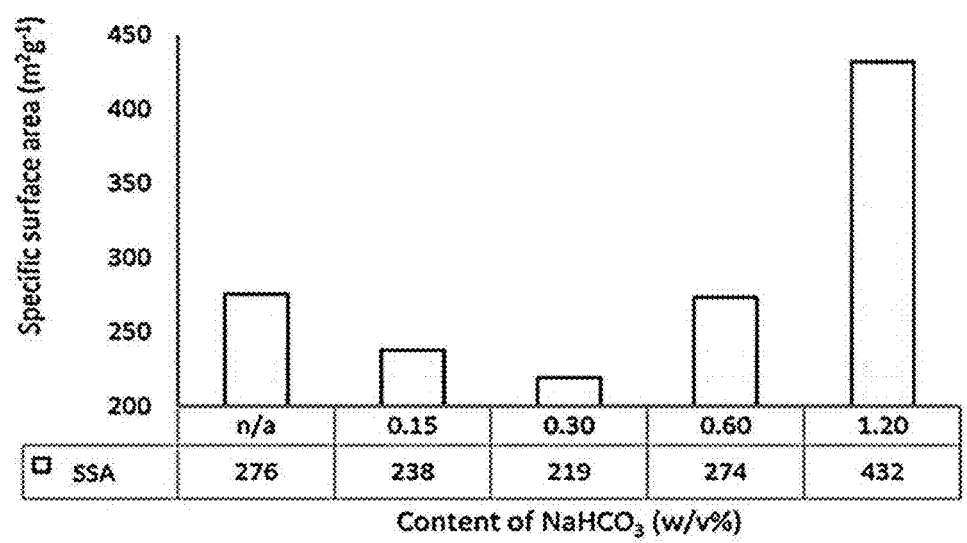
FIG. 7 shows the test results illustrating the specific surface area of the beads obtained according to Test Example 1.

Meanwhile, the tendency of density and swelling degree as shown in FIG. 5 and FIG. 6 conforms to the tendency of specific surface area as shown in FIG. 7. Referring to FIG. 7, the specific surface area of the beads is decreased as the amount of sodium bicarbonate ($NaHCO_3$) up to 0.3% (w/v) and is increased at a higher amount.

Example 3: Gas Permeability

The beads obtained according to Example 1 are subjected to a gas permeability test.

First, dinitrogen gas is injected to each type of beads obtained according to Example 1 at a flow rate of 1 L $N_2$/min. For reference, when treating highly concentrated wastewater by using anaerobic ammonium oxidizing bacteria, the flow rate of dinitrogen gas produced by the anaerobic ammonium oxidizing bacteria is about 0.44 L $N_2$/min.

Figure 8:
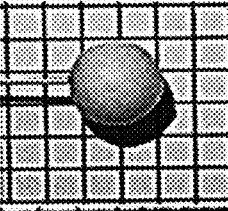
FIG. 8 shows the test results illustrating the expansion degree of the beads obtained according to Test Example 1 after injecting dinitrogen gas.
Figure 8:
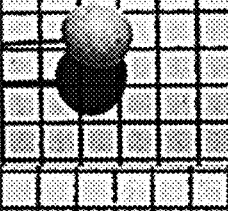
Figure 8:
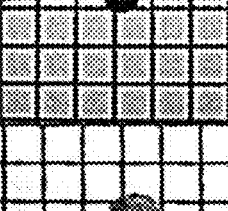
Figure 8:
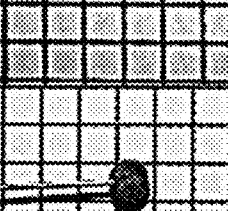
Figure 8:
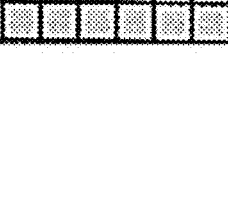

Referring to FIG. 8, in the case of the beads to which no sodium bicarbonate ($NaHCO_3$) is introduced, the beads have a diameter of 4.49 mm before the injection of dinitrogen gas. However, after the injection of dinitrogen gas, the beads are swelled to a diameter of 13.5 mm and are broken finally. On the contrary, when sodium bicarbonate ($NaHCO_3$) is introduced, the swelling degree of the beads is decreased as the amount of the sodium bicarbonate ($NaHCO_3$) introduced thereto is increased. When the amount of dinitrogen gas is 0.3% (w/v) or higher, the beads show an insignificant difference in diameter before and after the injection of dinitrogen gas. This suggests that dinitrogen gas in the beads is discharged effectively.

Example 4: Nitrogen Removal Property

To a reactor filled with influent, the beads obtained according to Example 1 are introduced and each type of beads is examined for nitrogen removal rate.

The operating conditions of the reactor are shown in the following Table 1 and the composition of the influent is shown in the following Table 2. In addition, the nitrogen removal rate (NRR) results of each type of beads depending on nitrogen loading rate (NLR) are shown in the following Table 3.

TABLE 1

| Operating Conditions of Reactor | |
| --- | --- |
| Reactor volume | 280 mL |
| Packing ratio | 42.7% |
| Agitation speed | 350 rpm |
| Hydraulic retention time | 8 hrs |

TABLE 2

| Composition of Influent | |
| --- | --- |
| $NH_4^+$—N | 50, 100, 150, 200, 300, 500 mg/L |
| $NO_2$—N | 50, 100, 150, 200, 300, 500 mg/L |
| $HCO_3^-$ | 72 mg/L |
| $KH_2PO_4$ | 6 mg/L |
| $MgCl \cdot 6H_2O$ | 12 mg/L |
| $CaCl_2 \cdot 2H_2O$ | 48 mg/L |
| Trace I, II | 1 mL/L |

TABLE 3

Nitrogen Removal Rate (NRR) of Each Type of Beads Depending on Nitrogen Loading Rate (NLR)

| Stage | Period (day) | NLR (kg · N/m³/d) | NRR (kg · N/m³/d) | | | |
| --- | --- | --- | --- | --- | --- | --- |
| | | | Control | 0.30 % (w/v) | 0.60 % (w/v) | 1.20 % (v/w) |
| 1 | 0-28 | 0.23 ± 0.03 | 0.10 ± 0.05 | 0.11 ± 0.05 | 0.11 ± 0.05 | 0.11 ± 0.05 |
| 2 | 29-36 | 0.32 ± 0.04 | 0.30 ± 0.05 | 0.30 ± 0.05 | 0.27 ± 0.07 | 0.07 ± 0.05 |
| 3 | 37-48 | 0.61 ± 0.01 | 0.54 ± 0.03 | 0.55 ± 0.05 | 0.55 ± 0.03 | — |
| 4 | 49-66 | 0.91 ± 0.02 | 0.82 ± 0.03 | 0.83 ± 0.03 | 0.83 ± 0.03 | — |
| 5 | 67-75 | 1.19 ± 0.02 | 1.04 ± 0.03 | 1.05 ± 0.02 | 1.08 ± 0.03 | — |
| 6 | 76-83 | 1.81 ± 0.01 | 1.67 ± 0.01 | 1.67 ± 0.01 | 1.69 ± 0.02 | — |
| 7 | 84-86 | 3.11 ± 0.01 | 1.93 ± 0.08 | 1.81 ± 0.02 | 2.25 ± 0.03 | — |
| 8 | 86-120 | 3.15 ± 0.01 | 1.00 ± 0.03 | 1.79 ± 0.02 | 2.75 ± 0.03 | — |

Referring to Table 3, in the case of the beads (see, "control" in Table 3) to which no sodium bicarbonate ($NaHCO_3$) is introduced, the nitrogen removal rate is reduced rapidly at the point of 86 days after the operation. After operating for 120 days, it can be seen that most of the beads are swelled or broken by nitrogen produced during the operation.

On the contrary, when the amount of sodium bicarbonate ($NaHCO_3$) is 0.3% or 0.6%, a higher nitrogen removal rate than that of "control" is obtained. Particularly, when the amount of sodium bicarbonate ($NaHCO_3$) is 0.6%, a very high nitrogen removal rate of 2.75 kg·N/m³/d or lower is obtained. Meanwhile, when the amount is 1.2%, no activity is shown due to the loss of bacteria after the reactor is operated for 36 days.

Based on the above results, it can be seen that when the amount of sodium bicarbonate ($NaHCO_3$) is 0.6%, particularly 0.5-0.7%, the highest nitrogen removal rate is obtained.

What is claimed is:

1. A method for preparing a carrier comprising ammonium oxidizing bacteria immobilized therein, the method comprising:
    preparing a polyvinyl alcohol (PVA)-alginate mixed solution containing PVA mixed with alginate;
    adding sludge containing ammonium oxidizing bacteria to the PVA-alginate mixed solution;
    adding sodium bicarbonate ($NaHCO_3$) to the PVA-alginate mixed solution and mixing the PVA-alginate mixed solution, the sludge containing ammonium oxidizing bacteria, and the sodium bicarbonate ($NaHCO_3$) to obtain a foaming-beading solution; and
    dropping the foaming-beading solution to a saturated boric acid solution to obtain beads including the sludge immobilized therein,
    wherein, in response to the foaming-beading solution being dropped to the saturated boric acid solution to obtain the beads including the sludge immobilized therein, the sodium bicarbonate ($NaHCO_3$) is decomposed to produce carbon dioxide ($CO_2$) which is discharged to the exterior of the beads to form pores in the beads.

2. The method for preparing a carrier comprising ammonium oxidizing bacteria immobilized therein according to claim 1, wherein the foaming-beading solution comprises the sodium bicarbonate ($NaHCO_3$) in an amount of 0.15-1.2% (w/v).

3. The method for preparing a carrier comprising ammonium oxidizing bacteria immobilized therein according to claim 1, wherein the foaming-beading solution comprises the sodium bicarbonate ($NaHCO_3$) in an amount of 0.5-0.7% (w/v).

4. The method for preparing a carrier comprising ammonium oxidizing bacteria immobilized therein according to claim 1, further comprising:
dipping the beads including the beads immobilized therein in a phosphoric acid solution to increase a mechanical strength.

5. The method for preparing a carrier comprising ammonium oxidizing bacteria immobilized therein according to claim 1, further comprising:
providing zeolite to the foaming-beading solution to control specific gravity of the beads.

6. The method for preparing a carrier comprising ammonium oxidizing bacteria immobilized therein according to claim 1, wherein the saturated boric acid solution is controlled to have a pH of 3-4.

7. The method for preparing a carrier comprising ammonium oxidizing bacteria immobilized therein according to claim 1, further comprising:
dipping the beads comprising the sludge immobilized therein in distilled water to induce swelling of the beads for the discharging of the sodium bicarbonate ($NaHCO_3$) and unreacted alginate remaining in the beads to the exterior of the beads.

8. The method for preparing a carrier comprising ammonium oxidizing bacteria immobilized therein according to claim 1, further comprising:
adding solid particles to the foaming-beading solution and mixing the solid particles with the foaming-beading solution,
wherein the solid particles are detached from the beads to form pores at portions where the solid particles are detached.

9. The method for preparing a carrier comprising ammonium oxidizing bacteria immobilized therein according to claim 8, wherein the solid particles comprise activated carbon.

10. The method for preparing a carrier comprising ammonium oxidizing bacteria immobilized therein according to claim 1, wherein the ammonium oxidizing bacteria comprise anaerobic ammonium oxidizing bacteria or aerobic ammonium oxidizing bacteria.

11. The method for preparing a carrier comprising ammonium oxidizing bacteria immobilized therein according to claim 10, wherein heterotrophic denitrifying bacteria is used to remove nitrite or nitrate in the form of dinitrogen gas.

12. A carrier comprising ammonium oxidizing bacteria immobilized therein obtained by the method as defined in claim 1.

13. A method for preparing a carrier comprising ammonium oxidizing bacteria immobilized therein, the method comprising:
providing a polyvinyl alcohol (PVA)-alginate mixed solution comprising PVA mixed with alginate;
providing sodium bicarbonate ($NaHCO_3$), zeolite, and sludge comprising ammonium oxidizing bacteria to the PVA-alginate mixed solution;
mixing the $NaHCO_3$, the zeolite, the sludge comprising ammonium oxidizing bacteria, and the PVA-alginate mixed solution to obtain a foaming-beading solution; and
dropping the obtained foaming-beading solution to a saturated boric acid solution to form beads including the sludge immobilized therein,
wherein the beads comprise pores formed in response to the $NaHCO_3$ being decomposed to produce carbon dioxide (CO2).

* * * * *